(12) United States Patent
Okubo et al.

(10) Patent No.: US 10,174,001 B2
(45) Date of Patent: Jan. 8, 2019

(54) CRYSTALS OF 5-CYCLOPROPYL-2-((1-(3-FLUOROBENZYL)-1H-INDOL-5-YL)AMINO)NICOTINIC ACID

(71) Applicant: FUJIFILM Toyama Chemical Co., Ltd., Chuo-ku, Tokyo (JP)

(72) Inventors: Yusuke Okubo, Toyama (JP); Tadashi Tanaka, Toyama (JP)

(73) Assignee: FUJIFILM Toyama Chemical Co., Ltd., Chuo-ku (JP)

( * ) Notice: Subject to any disclaimer, the term of this patent is extended or adjusted under 35 U.S.C. 154(b) by 0 days.

(21) Appl. No.: 15/755,281

(22) PCT Filed: Aug. 30, 2016

(86) PCT No.: PCT/JP2016/075318
§ 371 (c)(1),
(2) Date: Feb. 26, 2018

(87) PCT Pub. No.: WO2017/038815
PCT Pub. Date: Mar. 9, 2017

(65) Prior Publication Data
US 2018/0244647 A1   Aug. 30, 2018

(30) Foreign Application Priority Data

Aug. 31, 2015  (JP) ................................. 2015-170151

(51) Int. Cl.
*C07D 401/12* (2006.01)
(52) U.S. Cl.
CPC ........ *C07D 401/12* (2013.01); *C07B 2200/13* (2013.01)

(58) Field of Classification Search
CPC .......................... C07D 401/12; C07B 2200/13
See application file for complete search history.

(56) References Cited

U.S. PATENT DOCUMENTS 9,624,215 B2 *  4/2017  Tanaka ................. C07D 403/12
2015/0299189 A1  10/2015  Tanaka et al.

FOREIGN PATENT DOCUMENTS

WO     WO 2014/069510 A1     5/2014

OTHER PUBLICATIONS

International Search Report dated Nov. 22, 2016 in PCT/JP2016/075318 filed Aug. 30, 2016.
Teisuke Okano, "Shin Yakuzaigaku Soron (revised third edition)" Nankodo Co., Ltd., Apr. 10, 1987, 6 Pages.
Noriaki Hirayama, "Yuki Kagobutsu Sakusei Handbook—Genri to KnowHow—"Maruzen Co., Jul. 25, 2008, 28 Pages.

* cited by examiner

*Primary Examiner* — Timothy R Rozof
(74) *Attorney, Agent, or Firm* — Oblon, McClelland, Maier & Neustadt, L.L.P.

(57) ABSTRACT

Crystals of 5-cyclopropyl-2-((1-(3-fluorobenzyl)-1H-indol-5-yl)amino)nicotinic acid having diffraction peaks at diffraction angles (2θ) of 12.2±0.2, 17.2±0.2, 19.4±0.2, 24.1±0.2, and 27.1±0.2° or diffraction angles (2θ) of 12.9±0.2, 15.5±0.2, 21.2±0.2, 21.7±0.2, and 25.9±0.2° in powder x-ray diffraction have excellent stability, are easy to handle, and are useful as a drug substance of pharmaceuticals to be used in treatments such as the prevention or treatment of diseases involving keratinocyte hyperproliferation.

6 Claims, 3 Drawing Sheets

CRYSTALS OF 5-CYCLOPROPYL-2-((1-(3-FLUOROBENZYL)-1H-INDOL-5-YL)AMINO)NICOTINIC ACID

TECHNICAL FIELD

The present invention relates to crystals of 5-cyclopropyl-2-((1-(3-fluorobenzyl)-1H-indol-5-yl)amino)nicotinic acid useful for treatments such as prevention or therapy of diseases associated with overgrowth of keratinocyte.

BACKGROUND ART

5-Cyclopropyl-2-((1-(3-fluorobenzyl)-1H-indol-5-yl)amino)nicotinic acid (hereinafter, sometimes referred to as "Compound A") has an excellent antiproliferative activity on keratinocyte and is thus useful for treatments such as prevention or therapy of diseases associated with overgrowth of keratinocyte (Patent Document 1).

PRIOR ART DOCUMENTS

Patent Documents

Patent Document 1: WO 2014/069510 pamphlet

SUMMARY OF INVENTION

Technical Problem

Compound A as produced according to the production method described in Patent Document 1 was amorphous.

A subject of the present invention is to provide a novel crystal of Compound A having excellent stability and being useful for an active pharmaceutical ingredient of pharmaceuticals.

Solution to Problem

Under such circumstances, the present inventors conducted extensive studies and found that crystals of Compound A having diffraction peaks at diffraction angles (2θ) of 12.2±0.2, 17.2±0.2, 19.4±0.2, 24.1±0.2 and 27.1±0.2° in powder x-ray diffraction (hereinafter, sometimes referred to as "α-form crystal") have excellent stability, are easy to handle and are excellent as an active pharmaceutical ingredient of medicine.

Further, the inventors found that crystals of Compound A having diffraction peaks at diffraction angles (2θ) of 12.9±0.2, 15.5±0.2, 21.2±0.2, 21.7±0.2 and 25.9±0.2° in powder x-ray diffraction (hereinafter, sometimes referred to as "β-form crystal") have excellent stability, are easy to handle and are excellent as an active pharmaceutical ingredient of medicine, whereby the present invention has been completed.

More specifically, the present invention provides the followings.

<1>
A crystal of 5-cyclopropyl-2-((1-(3-fluorobenzyl)-1H-indol-5-yl)amino)nicotinic acid having diffraction peaks at diffraction angles (2θ) of 12.2±0.2, 17.2±0.2, 19.4±0.2, 24.1±0.2 and 27.1±0.2° in powder x-ray diffraction.

<2>
A crystal of 5-cyclopropyl-2-((1-(3-fluorobenzyl)-1H-indol-5-yl)amino)nicotinic acid having diffraction peaks at diffraction angles (2θ) of 12.9±0.2, 15.5±0.2, 21.2±0.2, 21.7±0.2 and 25.9±0.2° in powder x-ray diffraction.

<3>
A pharmaceutical composition comprising the crystal of <1> or <2>.

The present invention further provides the followings.

<4>
A method for producing a crystal of 5-cyclopropyl-2-((1-(3-fluorobenzyl)-1H-indol-5-yl)amino)nicotinic acid having diffraction peaks at diffraction angles (2θ) of 12.2±0.2, 17.2±0.2, 19.4±0.2, 24.1±0.2 and 27.1±0.2° in powder x-ray diffraction, the method including:

(1) a step of heat-dissolving a suspension containing 5-cyclopropyl-2-((1-(3-fluorobenzyl)-1H-indol-5-yl)amino)nicotinic acid and at least one solvent selected from alcohols, ethers, ketones and esters, and (2) a step of cooling the solution obtained in (1), wherein the alcohols are methanol, ethanol, propanol, 2-propanol or butanol;

the ethers are diethyl ether, diisopropyl ether, methyl tert-butyl ether, tetrahydrofuran or 1,4-dioxane;

the ketones are acetone, methyl ethyl ketone or methyl isobutyl ketone; and the esters are methyl acetate, ethyl acetate, propyl acetate, isopropyl acetate or butyl acetate.

<5>
The production method according to <4>, wherein the at least one solvent selected from alcohols, ethers, ketones and esters is at least one solvent selected from esters.

<6>
The production method according to <4>, wherein the at least one solvent selected from alcohols, ethers, ketones and esters is ethyl acetate.

<7>
A method for producing a crystal of 5-cyclopropyl-2-((1-(3-fluorobenzyl)-1H-indol-5-yl)amino)nicotinic acid having diffraction peaks at diffraction angles (2θ) of 12.9±0.2, 15.5±0.2, 21.2±0.2, 21.7±0.2 and 25.9±0.2° in powder x-ray diffraction, the method including:

(1) a step of preparing a solution containing 5-cyclopropyl-2-((1-(3-fluorobenzyl)-1H-indol-5-yl)amino)nicotinic acid, a base and at least one solvent selected from alcohols and esters, and (2) a step of adding an acid to the solution obtained in (1), wherein the alcohols are methanol, ethanol, propanol, 2-propanol or butanol;

the esters are methyl acetate, ethyl acetate, propyl acetate, isopropyl acetate or butyl acetate;

the base is sodium hydroxide, potassium hydroxide, sodium carbonate or potassium carbonate; and the acid is hydrochloric acid, sulfuric acid, nitric acid or phosphoric acid.

<8>
The production method according to <7>, wherein the alcohols are methanol, ethanol or propanol; and the esters are methyl acetate or ethyl acetate.

<9>
The production method according to <7> or <8>, wherein the base is sodium hydroxide or potassium hydroxide; and the acid is hydrochloric acid.

Advantageous Effects of Invention

The α-form crystal of the present invention has excellent stability, is easy to handle and useful for an active pharmaceutical ingredient of medicine.

The β-form crystal of the present invention has excellent stability, is easy to handle and useful for an active pharmaceutical ingredient of medicine.

DESCRIPTION OF EMBODIMENTS

Figure 1:
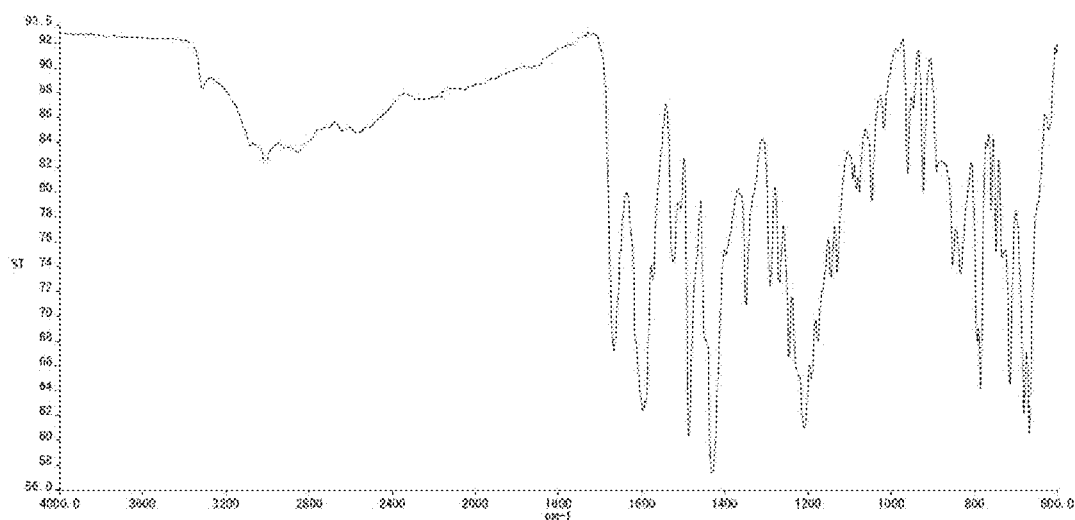
FIG. 1 is a drawing showing an example of the infrared absorption spectrum (ATR method) of the α-form crystal of Compound A.

The present invention is described in detail below.

In the present invention, % refers to mass % unless otherwise specified.

In the present invention, the terms have the following meanings unless otherwise specified.

The alcohols mean methanol, ethanol, propanol, 2-propanol or butanol.

The ethers mean diethyl ether, diisopropyl ether, methyl tert-butyl ether, tetrahydrofuran or 1,4-dioxane.

The ketones mean acetone, methyl ethyl ketone or methyl isobutyl ketone.

The esters mean methyl acetate, ethyl acetate, propyl acetate, isopropyl acetate or butyl acetate.

The aliphatic hydrocarbons mean hexane or cyclohexane.

The aromatic hydrocarbons mean benzene, chlorobenzene, dichlorobenzene, toluene or xylene.

The amides mean N,N-dimethylformamide, N,N-dimethylacetamide or N-methylpyrrolidone.

In general, the diffraction angle (2θ) in powder x-ray diffraction may cause an error within the range of ±0.2°. Accordingly, the "diffraction angles (2θ) of X°" used in the present invention means "diffraction angles (2θ) of ((X−0.2) to (X+0.2))°", unless otherwise specified. Thus, crystals having diffraction angles matching within an error range of ±0.2° are included in the present invention in addition to the crystals having precisely matching diffraction angles in powder x-ray diffraction.

In general, the value of wavelength (cm$^{-1}$) in the infrared absorption spectrum (ATR method) may cause an error within the range of ±2 cm$^{-1}$. Accordingly, the "wavelength Y cm$^{-1}$" used in the present invention means "wavelength ((Y−2) to (Y+2)) cm$^{-1}$", unless otherwise specified. Thus, crystals having wavelengths matching within an error range of ±2 cm$^{-1}$ at absorption peaks are included in the present invention in addition to crystals having precisely matching wavelengths at absorption peaks in the infrared absorption spectrum (ATR method).

The α-form crystal of the present invention is defined by the diffraction peak in powder x-ray diffraction.

The α-form crystals of the present invention have diffraction peaks at diffraction angles (2θ) of 12.2±0.2, 17.2±0.2, 19.4±0.2, 24.1±0.2 and 27.1±0.2° in powder x-ray diffraction.

The α-form crystal of the present invention is further defined by the absorption peak in the infrared absorption spectrum (ATR method).

The α-form crystals of the present invention have absorption peaks at the wavelengths of 1667±2, 1597±2, 1487±2 and 1430±2 cm$^{-1}$ in the infrared absorption spectrum (ATR method).

The β-form crystal of the present invention is defined by the diffraction peak in powder x-ray diffraction.

The β-form crystals of the present invention have diffraction peaks at diffraction angles (2θ) of 12.9±0.2, 15.5±0.2, 21.2±0.2, 21.7±0.2 and 25.9±0.2° in powder x-ray diffraction.

The β-form crystal of the present invention is further defined by the absorption peak in the infrared absorption spectrum (ATR method).

The β-form crystals of the present invention have absorption peaks at wavelengths of 1665±2, 1574±2, 1486±2 and 1449±2 cm$^{-1}$ in the infrared absorption spectrum (ATR method).

The methods for producing the α-form crystal and β-form crystal of the present invention will be described next.

The α-form crystal and β-form crystal can be produced by following, for example, the production methods below.

[Production Method 1] α-Form Crystal

A suspension of the amorphous of Compound A was heat-dissolved and then cooled to produce the α-form crystal.

Examples of the solvent used in this reaction include alcohols, ethers, ketones, esters, aliphatic hydrocarbons, aromatic hydrocarbons, amides, dimethyl sulfoxide, acetonitrile and water. These solvents may be used in combination.

A preferable solvent is at least one solvent selected from alcohols, ethers, ketones and esters, and at least one solvent selected from esters is more preferable, and ethyl acetate is further preferable.

The amount of the solvent used may be any amount of 1 to 100 times (v/w) and is preferably 15 to 20 times (v/w) the amount of amorphous of Compound A.

[Production Method 2] β-Form Crystal

To a suspension of the amorphous of Compound A or the α-form crystal, a base was added to be dissolved, and then an acid was added thereto to produce the β-form crystal.

Examples of the solvent used in this reaction include alcohols, ethers, ketones, esters, aliphatic hydrocarbons, aromatic hydrocarbons, amides, dimethyl sulfoxide, acetonitrile and water. These solvents may be used in combination.

A preferable solvent is at least one solvent selected from alcohols and esters, at least one solvent selected from methanol, ethanol, propanol, methyl acetate and ethyl acetate is more preferable, and a mixed solvent of methanol and ethyl acetate is further preferable.

The amount of the solvent used is preferably 1 to 100 times (v/w), more preferably 5 to 10 times (v/w) the amount of the amorphous of Compound A or the α-form crystal.

Examples of the base used in this reaction include sodium hydroxide, potassium hydroxide, sodium carbonate and potassium carbonate.

A preferable base is sodium hydroxide or potassium hydroxide, with sodium hydroxide being more preferable.

The amount of the base used is not particularly limited. It is preferable to add the base until the suspension is dissolved, it is more preferable to add the base so that pH is 6 to 10, and it is further preferable to add the base so that pH is 6 to 8.

The base may be added directly in the solid form but it is more preferable to add an aqueous solution of the base.

Examples of the acid used in this reaction include hydrochloric acid, sulfuric acid, nitric acid and phosphoric acid.

A preferable acid is hydrochloric acid.

The amount of the acid used is not particularly limited. It is preferable to add the acid so that pH is 3 to 5, and it is more preferable to add the acid so that pH is 4 to 5.

When the α-form crystal and the β-form crystal of the present invention are used as pharmaceutical products, adjuvants commonly used for formulating such as an excipient, a carrier and a diluent may suitably be mixed.

These can be orally or parenterally administered in the form of a tablet, a capsule, a powder, a syrup, a granule, a pill, a suspension, an emulsion, a liquid, a powdered formulation, a suppository, an eye drop, a nasal drop, an ear drop, a patch, an ointment, a lotion, a cream or an injection. Further, the administration method, the dose and the number of administration can be suitably selected in accordance with a patient's age, body weight and symptoms. Commonly, to an adult, these pharmaceutical products may be administered orally or parenterally (for example, an injection, an intravenous drip and administration to rectal region) in a single to several divided doses of 0.01 to 1000 mg/kg a day.

Usefulnesses of the α-form crystal and the β-form crystal of the present invention will be described next in reference to the following Test Examples.

Test Example 1: Solubility

The α-form crystal (about 100 mg) or the β-form crystal (about 100 mg) was suspended in various organic solvents (about 1 mL) and stirred for 24 hours. Impurities were filtered off using a membrane filter and the filtrate was analyzed by HPLC to determine the solubility.

The results are presented below.

TABLE 1

|  | α-Form crystal | β-Form crystal |
|---|---|---|
| Ethyl acetate | 19.7 | 16.8 |
| Isopropyl acetate | 11.5 | 9.8 |
| Acetone | 55.0 | 48.9 |
| Methyl ethyl ketone | 63.1 | 55.3 |
| Methyl tert-butyl ether | 10.1 | 8.1 |
| Ethanol | 8.8 | 6.8 |
| 2-Propanol | 3.5 | 3.0 |
| Acetonitrile | 3.1 | 2.7 |

(mg/mL)

The solubility of the β-form crystal was lower than the solubility of the α-form crystal. In general, the lower the solubility is, the better the stability is (Separation Process Engineers Series 5, revised Wakariyasui Shouseki Sousa (in Japanese) (Easy Crystallization Engineering), co-authored by Kubota Noriaki and Matsuoka Masakuni, 2003, The Society of Separation Process Engineers, Japan).

The β-form crystal was more stable than the α-form crystal.

Test Example 2: Physical Stability

The α-form crystal (1 part by weight) and the β-form crystal (1 part by weight) were mixed, suspended in a solvent (ethyl acetate/ethanol=5/1.5 parts by weight) and stirred at 26, 70 or 100° C.

Sampling was carried out over time and crystal forms were measured by the infrared absorption spectrum.

The results are presented below.

TABLE 2

|  | 26° C. | 70° C. | 100° C. |
|---|---|---|---|
| 0 hr | α + β | α + β | α + β |
| 0.5 hr | α + β | β | β |
| 2 hr | β | — | — |

The α-form crystal transitioned to the β-form crystal.

The β-form crystal was more stable than the α-form crystal.

Test Example 3: Hygroscopicity

The α-form crystal and the β-form crystal were preserved under the conditions of 25° C. and a relative humidity of 75 or 97%.

Sampling was carried out over time and the weights of crystals were measured to determine rates of weight changes. Additionally, crystal forms were measured by the infrared absorption spectrum.

The results are presented below.

Rate of weight change (%)=$((B-A)/A) \times 100$

A: Crystal weight before the test started
B: Crystal weight after the test started

TABLE 3

| 25° C. 75% RH | | | | |
|---|---|---|---|---|
| | α-Form crystal | | β-Form crystal | |
| | Crystal form | Rate of weight change (%) | Crystal form | Rate of weight change (%) |
| 0 hr | α | 0.00 | β | 0.00 |
| 2 weeks | α | 0.08 | β | 0.07 |
| 4 weeks | α | 0.08 | β | 0.07 |
| 8 weeks | α | 0.24 | β | 0.20 |
| 12 weeks | α | 0.22 | β | 0.18 |

TABLE 4

| 25° C. 97% RH | | | | |
|---|---|---|---|---|
| | α-Form crystal | | β-Form crystal | |
| | Crystal form | Rate of weight change (%) | Crystal form | Rate of weight change (%) |
| 0 hr | α | 0.00 | β | 0.00 |
| 2 weeks | α | 0.13 | β | 0.10 |
| 4 weeks | α | 0.17 | β | 0.11 |
| 8 weeks | α | 0.38 | β | 0.26 |
| 12 weeks | α | 0.32 | β | 0.25 |

Crystal transition was not detected.

The rates of weight changes of the α-form crystal and the β-form crystal were less than 0.5%. The α-form crystal and the β-form crystal were stable.

Test Example 4: Stability

The α-form crystal and the β-form crystal were preserved under the conditions of 40 or 60° C. and a relative humidity of 75%.

Twelve weeks after the test started, the purity was measured by HPLC. Additionally, crystal forms were measured by the infrared absorption spectrum.

The results are presented below.

HPLC Measurement conditions
Measurement wavelength: 270 nm
Column: Ascentis Express C18, inner diameter 3.0 mm×length 150 mm
Column temperature: 40° C.
Flow rate: 2.0 mL/min
Mobile phase: 0.1% phosphoric acid/(acetonitrile/water=60/40) solution

TABLE 5

40° C. 75% RH

| | α-Form crystal | | β-Form crystal | |
|---|---|---|---|---|
| | Crystal form | Purity (%) | Crystal form | Purity (%) |
| 0 hr | α | 99.4 | β | 99.6 |
| 12 weeks | α | 99.5 | β | 99.7 |

TABLE 6

60° C. 75% RH

| | α-Form crystal | | β-Form crystal | |
|---|---|---|---|---|
| | Crystal form | Purity (%) | Crystal form | Purity (%) |
| 0 hr | α | 99.4 | β | 99.6 |
| 12 weeks | α | 99.5 | β | 99.7 |

Crystal transition was not detected.
Change in the purity was not detected.
Both crystals were stable.

EXAMPLES

The crystals of the present invention will be described next in reference to Reference Examples and Examples, but the present invention is not limited thereto.

The purification by column chromatography was carried out using medium pressure liquid chromatography YFLC-Wprep2XY.N (YAMAZEN CORPORATION).

For the carrier for silica gel column chromatography, Silica Gel 60 (spherical) of KANTO CHEMICAL, CO., INC. was used.

The mixing ratio of eluents is a volume ratio. For example, the "gradient elution of hexane:ethyl acetate=100:0 to 50:50" means that eluents of 100% hexane/0% ethyl acetate was ultimately changed to the eluents of 50% hexane/50% ethyl acetate.

$^1$H-NMR spectrum was measured using tetramethylsilane as an internal standard by JNM-AL400 (JEOL Ltd.) and all δ values were presented in ppm.

Abbreviations in the NMR measurement mean as follows.
s: Singlet
d: Doublet
m: Multiplet
DMSO-$D_6$: Hexadeuterodimethyl sulfoxide MS Spectrum was measured using ACQUITY SQD LC/MS System (Waters Corporation).

Infrared absorption spectrum was measured in accordance with Japanese Pharmacopoeia, General Tests, Infrared absorption spectrum Attenuated Total Reflection (ATR method) using Spectrum One (PerkinElmer).

Powder x-ray diffraction was measured using Ultima IV (Rigaku Corporation) under the following conditions.
(Measurement Conditions)
x-Ray used: CuKα
Tube voltage: 40 kV
Tube current: 40 mA
Scan axis: 2θ

Water content was measured using a Karl Fischer Moisture Titrate CA-100 (Mitsubishi Chemical Corporation).

Purity is a high performance liquid chromatography (HPLC) area %. Note that the measurement of HPLC was carried out using Prominence (Shimadzu Corporation) under the following conditions.
(Measurement Conditions)
Measurement wavelength: 270 nm
Column: Ascentis Express C18, inner diameter 3.0 mm×length 150 mm
Column temperature: 40° C.
Flor rate: 2.0 mL/min
Mobile phase: 0.1% phosphoric acid/(acetonitrile/water=60/40) solution Reference Example 1: Amorphous Compound A Amorphous Compound A was produced by the production method described in Patent Document 1.

To a mixed solution of 2 mL of methanol of 5-cyclopropyl-2-(2,2,2-trifluoro-N-(1-(3-fluorobenzyl)-1H-indol-5-yl)aceteamide)nicotinate obtained by the production method described in Patent Document 1 and 4 mL of tetrahydrofuran, 1 mL of a 1 mol/L sodium hydroxide aqueous solution was added, and the mixture was heated to reflux for 1 hour. The reaction mixture was cooled to room temperature, and then the solvent was distilled off under reduced pressure. Ethyl acetate and water were added to the obtained residue, and pH was adjusted to 2.5 to 3.0 with 1 mol/L hydrochloric acid. The organic layer was separately collected, dried over anhydrous magnesium sulfate and the solvent was distilled off under reduced pressure. The obtained residue was purified by silica gel column chromatography (gradient elution of hexane:ethyl acetate=50:50 to 0:100), ethyl acetate and hexane were added thereto, and the solid matter was collected by filtration, thereby obtaining 22 mg of Compound A in the form of yellow solid. The obtained Compound A was amorphous.

Figure 5:
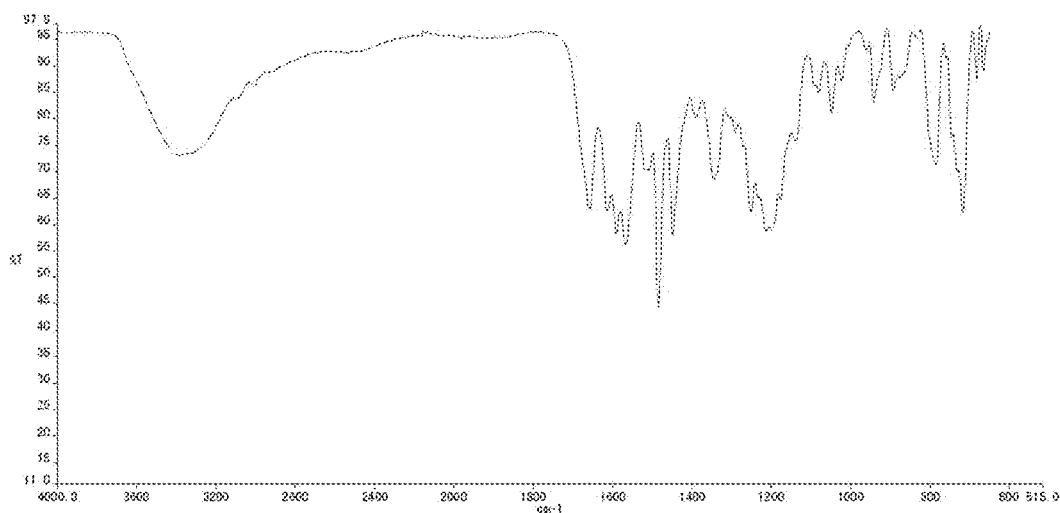
FIG. 5 is a drawing showing an example of the infrared absorption spectrum (ATR method) of the amorphous of Compound A.
Figure 6:
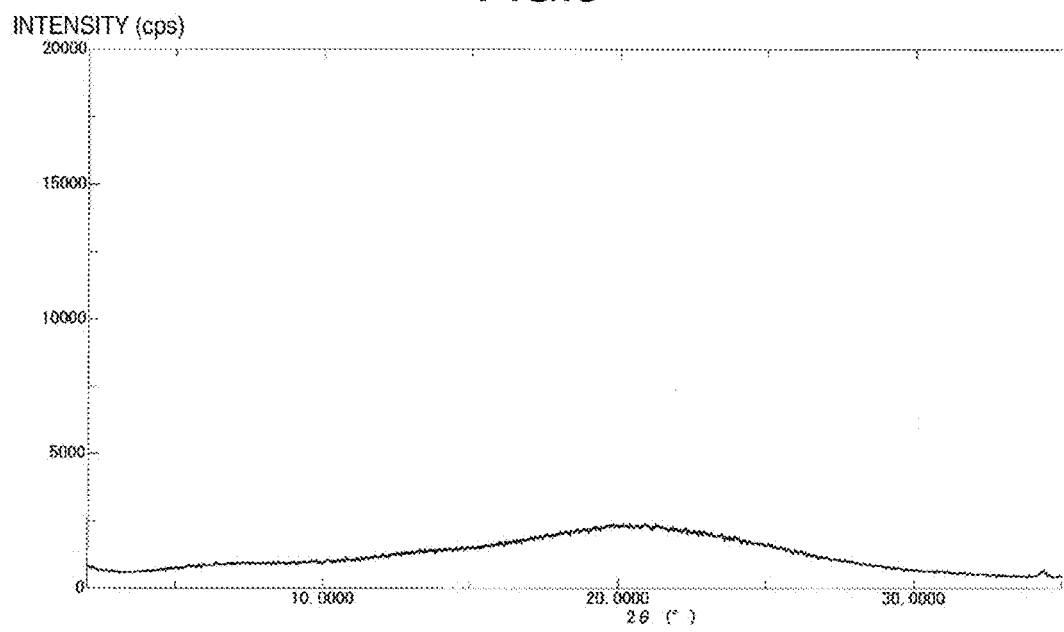
FIG. 6 is a drawing showing an example of a powder x-ray diffraction pattern of the amorphous of Compound A.

The infrared absorption spectrum (ATR method) is shown in FIG. 5 and the powder x-ray diffraction pattern is shown in FIG. 6.

$^1$H-NMR (DMSO-$D_6$) δ: 0.61-0.68 (2H, m), 0.86-0.96 (2H, m), 1.85-1.96 (1H, m), 5.43 (2H, s), 6.45 (1H, d, J=3.3 Hz), 6.95-7.20 (4H, m), 7.32-7.40 (2H, m), 7.50 (1H, d, J=3.3 Hz), 7.87 (1H, d, J=2.6 Hz), 7.97 (1H, d, J=2.0 Hz), 8.18 (1H, d, J=2.6 Hz), 10.10 (1H, s).

MS (ESI, m/z): 402 (M+H)

Example 1: α-Form Crystal

A mixture of 4.5 g of the amorphous Compound A obtained by the same method as in Reference Example 1 and 80.0 mL of ethyl acetate was stirred until dissolved under heat reflux. The solution was cooled to 64° C. to confirm the precipitation of the crystal and then cooled to room temperature over a period of 1 hour. Subsequently, the mixture was cooled to 5° C. and stirred for 1 hour, and then the solid matter was collected by filtration, thereby obtaining 4.08 g of the α-form crystal.

Figure 2:
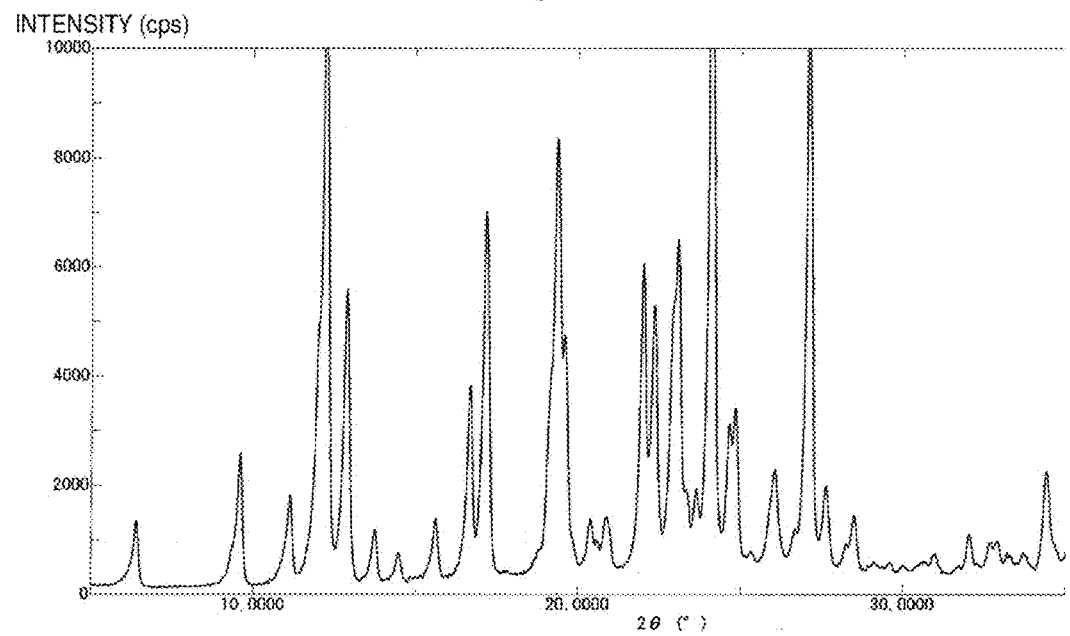
FIG. 2 is a drawing showing an example of a powder x-ray diffraction pattern of the α-form crystal of Compound A.

The infrared absorption spectrum (ATR method) is shown in FIG. 1 and the powder x-ray diffraction pattern is shown in FIG. 2 and Table 7.

IR (ATR): 1667, 1597, 1487, 1430 cm$^{-1}$

TABLE 7

| 2θ | d (Å) | Relative intensity (%) |
|---|---|---|
| 12.23 | 7.23 | 83 |
| 12.86 | 6.88 | 37 |
| 17.16 | 5.16 | 47 |
| 19.35 | 4.58 | 55 |
| 21.97 | 4.04 | 39 |
| 22.32 | 3.98 | 33 |
| 22.88 | 3.88 | 31 |
| 23.06 | 3.85 | 39 |
| 24.10 | 3.69 | 100 |
| 27.08 | 3.29 | 77 |

Example 2: β-Form Crystal

To a mixed solution of 25.0 mL of ethyl acetate containing 4.06 g of the α-form crystal obtained in Example 1 and 5.0 mL of methanol, a 25% sodium hydroxide aqueous solution was added to adjust pH to 7.4, and then the solution was stirred until dissolved. Concentrated hydrochloric acid was added to adjust pH to 4.6 and stirred at 30° C. After the precipitation of crystal was confirmed, the mixture was stirred for 0.5 hours under heat reflux. The mixture was cooled to room temperature and then the solid matter was collected by filtration, thereby obtaining 3.24 g of the β-form crystal.

Figure 3:
FIG. 3 is a drawing showing an example of the infrared absorption spectrum (ATR method) of the β-form crystal of Compound A.
Figure 4:
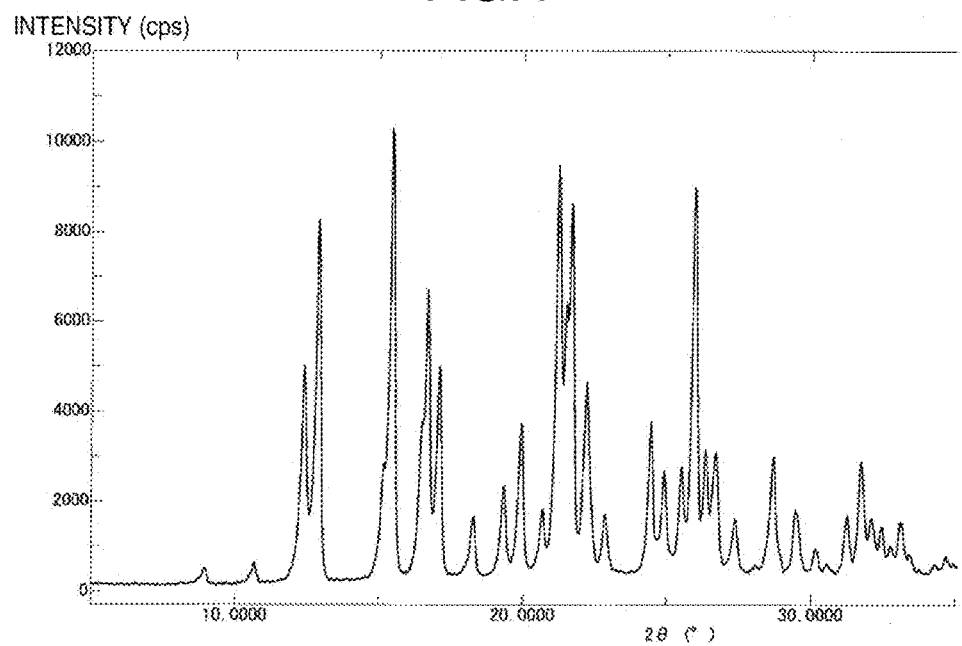
FIG. 4 is a drawing showing an example of a powder x-ray diffraction pattern of the β-form crystal of Compound A.

The infrared absorption spectrum (ATR method) is shown in FIG. 3 and the powder x-ray diffraction pattern is shown in FIG. 4 and Table 8.

IR (ATR): 1665, 1574, 1486, 1449 cm$^{-1}$

TABLE 8

| 2θ | d (Å) | Relative intensity (%) |
|---|---|---|
| 12.37 | 7.15 | 46 |
| 12.86 | 6.88 | 79 |
| 15.45 | 5.73 | 100 |
| 16.67 | 5.31 | 64 |
| 17.07 | 5.19 | 48 |
| 21.18 | 4.19 | 87 |
| 21.44 | 4.14 | 53 |
| 21.65 | 4.10 | 79 |
| 22.18 | 4.00 | 40 |
| 25.93 | 3.43 | 85 |

INDUSTRIAL APPLICABILITY

The crystals of the present invention have excellent stability, are easy to handle and useful for an active pharmaceutical ingredient of pharmaceuticals.

The invention claimed is:

1. A crystal of 5-cyclopropyl-2-((1-(3-fluorobenzyl)-1H-indol-5-yl)amino)nicotinic acid having diffraction peaks at diffraction angles (2θ) of 12.2±0.2, 17.2±0.2, 19.4±0.2, 24.1±0.2 and 27.1±0.2° in powder x-ray diffraction.

2. A crystal of 5-cyclopropyl-2-((1-(3-fluorobenzyl)-1H-indol-5-yl)amino)nicotinic acid having diffraction peaks at diffraction angles (2θ) of 12.9±0.2, 15.5±0.2, 21.2±0.2, 21.7±0.2 and 25.9±0.2° in powder x-ray diffraction.

3. A pharmaceutical composition comprising the crystal of claim 1 and a pharmaceutically acceptable adjuvant.

4. A pharmaceutical composition comprising the crystal of claim 2 and a pharmaceutically acceptable adjuvant.

5. The pharmaceutical composition of claim 3, wherein the adjuvant is at least one selected from the group consisting of an excipient, a carrier and a diluent.

6. The pharmaceutical composition of claim 4, wherein the adjuvant is at least one selected from the group consisting of an excipient, a carrier and a diluent.

* * * * *

UNITED STATES PATENT AND TRADEMARK OFFICE
CERTIFICATE OF CORRECTION

PATENT NO. : 10,174,001 B2  
APPLICATION NO. : 15/755281  
DATED : January 8, 2019  
INVENTOR(S) : Yusuke Okubo et al.

Page 1 of 1

It is certified that error appears in the above-identified patent and that said Letters Patent is hereby corrected as shown below:

On the Title Page

Item (73), the Assignee information should read:  
--(73) Assignee: FUJIFILM Toyama Chemical Co., Ltd, Chuo-ku (JP); Fujifilm Corporation, Minato-ku (JP)--

Signed and Sealed this  
Fifth Day of November, 2019

Andrei Iancu  
*Director of the United States Patent and Trademark Office*